United States Patent [19]

Giesselmann et al.

[11] 4,206,136

[45] Jun. 3, 1980

[54] PROCESS FOR THE PRODUCTION OF METHYLISOCYANATE

[75] Inventors: Günter Giesselmann, Heusenstamm; Kurt Günther, Rodenbach; Werner aus der Fünten, Hanau, all of Fed. Rep. of Germany

[73] Assignee: Deutsche Gold- und Silber-Scheideanstalt Vormals Roessler, Frankfurt am Main, Fed. Rep. of Germany

[21] Appl. No.: 51,407

[22] Filed: Jun. 25, 1979

[30] Foreign Application Priority Data

Jun. 28, 1978 [DE] Fed. Rep. of Germany ....... 2828259

[51] Int. Cl.$^2$ ............................................. C07C 118/00
[52] U.S. Cl. ................................................. 260/453 P
[58] Field of Search ..................................... 260/453 P

[56] References Cited

U.S. PATENT DOCUMENTS 2,771,483  11/1956  Bieber .............................. 260/453 P

FOREIGN PATENT DOCUMENTS 48-1651  1/1973  Japan .

OTHER PUBLICATIONS

Slotta et al., Berichte, vol. 58, pp. 1320–1323 (1925).

*Primary Examiner*—Dolph H. Torrence
*Attorney, Agent, or Firm*—Cushman, Darby & Cushman

[57] ABSTRACT

Methyl isocyanate is prepared by reacting an alkali cyanate with dimethyl sulfate in the presence of an alkaline earth metal oxide and in an inert organic liquid. There can also be present an alkali metal or alkaline earth metal salt.

19 Claims, No Drawings

PROCESS FOR THE PRODUCTION OF METHYLISOCYANATE

BACKGROUND OF THE INVENTION

The invention is directed to a process for the production of methyl isocyanate by reaction of an alkali cyanate with dimethyl sulfate.

It is known to produce methyl isocyanate through the action of alkali cyanates on methyl halides. The reaction takes place with methyl chloride, methyl bromide or methyl iodide in the presence of dimethyl formamide or N-methyl pyrrolidone and in the presence of a nitrogen compound, such as pyridine and a hydroxy compound such as phenol (Japan published application No. 089090) or with methyl chloride in the presence of dimethyl formamide under super atmospheric pressure (Japanese OS No. 089810). A disadvantage in this process is that either long reaction times are required or superatmospheric pressure is necessary.

It is also known to form methyl isocyanate in the thermal decomposition of methylcarbamic acid chloride in inert organic solvents. (Urbach, U.S. Pat. No. 3,969,389). Relatively good yields are produced but long reaction times are required so that the space-time-yield is small. Besides this process presupposes the production of methylcarbamic acid chloride by the reaction of phosgene on methylamine hydrochloride so that the process all together is expensive.

Finally it is known to produce methyl isocyanate by the action of dimethyl sulfate on potassium cyanates. The reaction is carried out in the presence of inert materials, especially in the presence of anhydrous sodium carbonate. The yield is merely 50 to 55% (Slotta, Berichte Vol. 58 (1925) pages 1320–1323).

SUMMARY OF THE INVENTION

There has now been found a process for the production of methyl isocyanate by reaction of an alkali cyanate with dimethyl sulfate in the presence of an inert substance wherein the reaction is carried out in the presence of an alkaline earth metal oxide in an inert organic liquid. In this process there are produced yields of over 80% in relatively short reaction times.

As alkali cyanate there is preferably used sodium cyanate, potassium cyanate or a mixture of sodium cyanate and potassium cyanate. Especially suited is potassium cyanate or sodium cyanate which contains at least 20 mol %, especially 25 to 40 mol % of potassium cyanate.

According to the invention the reaction of the alkali cyanate takes place with the dimethyl sulfate in the presence of an oxide of an alkaline earth metal. Preferably there is used magnesium oxide and especially calcium oxide. There also can be used strontium oxide and barium oxide, for example. There can also be added mixtures of oxides, especially mixtures which consist essentially of calcium oxide.

Besides it can be advantageous to add other materials which behave inertly. As such, for example there can be used the salts of the alkali metals and alkaline earth metals, especially the alkali metal and alkaline earth metal carbonates as well as preferably the halides, especially the chlorides of the alkaline earth metals. Thus for example there can be added sodium chloride, potassium chloride, sodium carbonate, potassium carbonate, sodium bromide, sodium iodide, potassium bromide, potassium iodide, magnesium carbonate, magnesium chloride, magnesium bromide, magnesium iodide, calcium carbonate, calcium chloride, calcium bromide, calcium iodide, strontium carbonate, strontium chloride, strontium bromide, strontium iodide, barium carbonate, barium chloride, barium bromide or barium iodide. Preferably there are used salts as those of the alkali metal sodium and especially potassium and those of the alkaline earth metal magnesium and especially calcium.

According to the invention the reaction takes place in a inert organic liquid. (This is another difference from Slotta who does not have an inert organic liquid present). As liquids there can be used for example aliphatic or cycloaliphatic hydrocarbons, such as gasoline fractions boiling between 140° and 220° C. and decalin, aromatic hydrocarbons such as ethyl benzene, isopropyl benzene, methyl naphthalene, o-, m- and p-xylene, o-, m- and p-cymene, aliphatic and cycloaliphatic halogenated, especially chlorinated hydrocarbons such as tetrachloroethane, pentachloroethane, tetrachloroethylene, or aromatic halogenated, especially chlorinated, hydrocarbons, such as chlorobenzene 1,2-difluorobenzene, 1,3-difluorobenzene, 1,4-difluorobenzene, 1,2-dichlorobenzene, 1,3-dichlorobenzene, 1,4-dichlorobenzene, 1,2,4-trichlorobenzene, alphachloronaphthalene, or their mixtures with each other.

Expecially suited are 1,2-dichlorobenzene, 1,3-dichlorobenzene, 1-4-dichlorobenzene and 1,2,4-trichlorobenzene or their mixtures with each other.

The reaction conditions such as temperature and pressure and the molar ratios of the reacting materials are in a given case to a certain extent dependent upon one another and are adjusted in a given case depending on the type of materials used and particularly according to the type of organic liquid in which the reaction is carried out.

In general for the reaction there are chosen temperatures between about 100° and 200° C. In most cases there are preferred temperatures between 150° and 200° C. especially between 165° and 185° C. It is generally advantageous to operate at pressures between about 0.5 and 4 bar, particularly at normal pressure, however, there can also be used lower or higher pressure, although it is suitable in order to be able to use simple apparatus not to use substantially deviating pressure.

It is especially advantageous in most cases to carry out the reaction in such manner that the methyl isocyanate formed is always directly removed from the reaction mixture. For this purpose it is generally suitable to carry out the reaction at the boiling temperature of the reaction mixture. Preferably therefore the reaction is carried out in organic liquids or in a given case in mixtures of organic liquids whose boiling point at the pressure chosen is in the range of the reaction temperature.

The molar ratio of alkali cyanate to dimethyl sulfate can be widely varied at random, both stoichiometric as well as below or above stoichiometric amounts can be chosen. Generally it is advantageous per mol of alkali cyanate to add about 1 to 2 mols of dimethyl sulfate. Preferably there are used about 0.7 to 1.5 mol, especially 0.7 to 1.0 mol of the dimethyl sulfate.

The alkaline earth metal oxide can be present in the reaction in widely varying amount as desired. In most cases it is suitable that there be present per mol of alkali cyanate at least about 0.05 mol, preferably about 0.1 to 1.5 mol, especially 0.2 to 0.3 mol of oxide.

Also the salt of the alkali metal or alkaline earth metal can be present in widely varying amount as desired. In most cases, however, it is suitable per mol of alkali cyanate not be have present more than a total of about 1 mol of salt. In a given case there is used the alkaline earth metal halide preferably in an amount of about 0.005 to 0.2 mol, especially 0.01 to 0.05 mol.

According to the invention the reaction is carried out in an inert organic liquid. In what amount this liquid is added depends to a certain extent on the type of liquid and the type and relative proportions of the remaining materials. Generally there is used per part by weight of alkali cyanate at least about 1 part by weight of the liquid. In most cases it is advantageous per part by weight of alkali cyanate to have present about 2 to 100 parts by weight of liquid. Preferably there are 3 to 6 parts by weight of the liquid per part by weight of alkali cyanate.

The alkali cyanate, as well as the alkaline earth metal oxide and the, in a given case, provided alkali metal and alkaline earth metal compounds are introduced as solids. It is generally advantageous to use these materials in the finest possible state of subdivision.

Furthermore, it is advantageous to carry out the reaction in the absence of water. Therefore it is suitable to add all materials in water free form. In the case where individual materials contain water, it is a preferred procedure to introduce the materials with the exception of the dimethyl sulfate into the organic liquid, to heat this mixture so that the water is driven off, in a given case as an azeotropic mixture with the organic liquid used, and then to add the dimethyl sulfate in water free form.

Unless otherwise indicated all parts and percents are by weights.

The process can comprise, consist essentially of or consist of the steps set forth with the materials set forth.

DESCRIPTION OF THE PREFERRED EMBODIMENTS

EXAMPLE 1

There were used 164 grams (2 mols) of potassium cyanate (99 percent pure), 20 grams (0.4 mol) of calcium oxide and 4 grams (0.04 mol) of calcium chloride. The materials were water free and finely ground. They were introduced into 500 ml of 1,2-dichlorobenzene. To remove any residue of water present the mixture was held at the boiling temperature until 10 ml of the dichlorobenzene was distilled off. Then, while the mixture under a reflux condenser heated at 45° C. was held at the boiling temperature (172° to 177° C.) and intensively stirred there were gradually dropped in during the course of 90 minutes 189 grams (1.5 mols) of water free dimethyl sulfate. The methyl isocyanate formed was continuously distilled off. It formed a water clear, colorless liquid boiling at 37° to 38° C. The yield amounted to 102 grams, corresponding to 89% based on the potassium cyanate added.

EXAMPLE 2

The procedure was the same as in Example 1 but there were used 93 grams (1.4 mols) of sodium cyanate (98% pure), 49 grams (0.4 mol) of potassium cyanate (99% pure), 20 grams (0.4 mol) of calcium oxide, 9 grams (0.08 mol) of sodium carbonate and 4 grams (0.04 mol) of calcium chloride and the 189 grams of dimethyl sulfate were dropped in during the course of 110 minutes. The yield of methyl isocyanate was 99 grams, corresponding to 87% based on the alkali cyanate added.

EXAMPLE 3

The procedure was the same as in Example 1 but there were used 164 grams (2 mols) of potassium cyanate (99% pure) and 20 grams (0.4 mol) of calcium oxide. As organic liquid there was added 500 ml of a mixture of alkyl benzene which had a boiling range of 180° to 190° C. and the dimethyl sulfate was dropped in the course of 30 minutes. The reaction mixture by that time had a temperature of 183° to 185° C. The yield of methyl isocyanate was 92 grams, corresponding to 81% based on the potassium cyanate added.

EXAMPLE 4

The procedure was the same as in Example 1 but the calcium chloride was omitted and as the organic liquid there was added 500 ml of a mixture of 1.5 parts by volume of 1,2-dichlorobenzene and 1.0 part by volume of 1,2,4-trichlorobenzene. The reaction took place at 181° to 183° C. The yield was 94 grams, corresponding to 83% based on the potassium cyanate added.

There is hereby incorporated by reference the entire disclosure of German priority application No. P 28 28 259.9.

What is claimed is:

1. A process for the production of methyl isocyanate comprising reacting an alkali metal cyanate with dimethyl sulfate in the presence of an alkaline earth metal oxide and in an inert organic liquid.

2. A process according to claim 1 wherein the alkali metal cyanate is sodium cyanate, potassium cyanate or a mixture of sodium and potassium cyanate.

3. A process according to claim 2 wherein the alkali metal cyanate contains at least 20 mol% of potassium cyanate.

4. A process according to claim 3 wherein the alkali metal cyanate is all potassium cyanate.

5. A process according to claim 3 wherein the alkali metal cyanate is sodium cyanate containing 25 to 40 mol% potassium cyanate.

6. A process according to claim 2 wherein the alkaline earth metal oxide is magnesium oxide or calcium oxide.

7. A process according to claim 6 wherein the alkaline earth metal oxide is calcium oxide.

8. A process according to claim 6 wherein there is used about 0.7 to 2 mols of dimethyl sulfate and 0.05 to 1.5 mols of alkaline earth metal oxide per mol of alkali cyanate.

9. A process according to claim 6 wherein there is also employed a salt of an alkali metal or alkaline earth metal.

10. A process according to claim 9 wherein the salt is a carbonate or halide.

11. A process according to claim 10 wherein the salt is a carbonate or chloride.

12. A process according to claim 10 wherein there is used about 0.7 to 2 mols of dimethyl sulfate, 0.05 to 1.5 mols of alkaline earth metal oxide and 0.005 to 1 mol of salt per mol of alkali metal cyanate.

13. A process according to claim 10 wherein the salt is calcium chloride.

14. A process according to claim 2 wherein the inert liquid is a hydrocarbon or halohydrocarbon.

15. A process according to claim 14 wherein the inert liquid is a hydrocarbon or chlorinated hydrocarbon.

16. A process according to claim 15 wherein the inert liquid is an aromatic hydrocarbon or chlorinated aromatic hydrocarbon.

17. A process according to claim 16 wherein the inert organic liquid is dichlorobenzene of 1,2,4-trichlorobenzene or a mixture thereof.

18. A process according to claim 2 wherein the reaction is carried out at 165° to 185° C.

19. A process according to claim 2 comprising removing the methyl isocyanate formed immediately from the reaction mixture as it is formed.

* * * * *